(12) United States Patent
Criddle et al.

(10) Patent No.: US 8,030,021 B2
(45) Date of Patent: Oct. 4, 2011

(54) USE OF SELECTION PRESSURES TO ENABLE MICROBIAL BIOSYNTHESIS OF POLYHYDROXYALKANOATES FROM ANAEROBIC DEGRADATION PRODUCTS

(75) Inventors: Craig S. Criddle, Redwood City, CA (US); Allison J. Pieja, Menlo Park, CA (US)

(73) Assignee: The Board of Trustees of the Leland Standford Junior University, Palo Alto, CA (US)

( * ) Notice: Subject to any disclaimer, the term of this patent is extended or adjusted under 35 U.S.C. 154(b) by 344 days.

(21) Appl. No.: 12/456,988

(22) Filed: Jun. 24, 2009

(65) Prior Publication Data

US 2009/0317879 A1     Dec. 24, 2009

Related U.S. Application Data

(60) Provisional application No. 61/133,056, filed on Jun. 24, 2008.

(51) Int. Cl.
   *C12P 39/00* (2006.01)
   *C12P 7/64* (2006.01)
(52) U.S. Cl. .......................... 435/42; 435/135; 435/170
(58) Field of Classification Search ................ 435/42, 435/135, 170
   See application file for complete search history.

(56) References Cited

U.S. PATENT DOCUMENTS

| | | |
|---|---|---|
| 6,982,161 B1 | 1/2006 | Herrema |
| 2007/0202581 A1 | 8/2007 | Herrema et al. |
| 2010/0190221 A1 | 7/2010 | Herrema et al. |
| 2010/0255540 A2 | 10/2010 | Herrema et al. |

FOREIGN PATENT DOCUMENTS

WO    WO/2007/024255    3/2007

OTHER PUBLICATIONS

Verlinden et al. Bacterial synthesis of biodegradable polyhydroxyalkanoates. Journal of Applied Microbiology ISSN 1364-5072, 2007.
Dias et al. Recent Advances in Polyhydroxyalkanoate Production by Mixed Aerobic Cultures: From the Substrate to the Final Product. Macromol. Biosci. 2006, 6, 885-906.

*Primary Examiner* — Herbert J Lilling
(74) *Attorney, Agent, or Firm* — Lumen Patent Firm

(57) ABSTRACT

A method for inexpensive and efficient PHA biosynthesis includes operating a sequencing bioreactor in alternating phases of nutrient deprivation and carbon feedstock deprivation to select for robust PHA-producing microbes. Preferably, the bioreactor is operated in a non-sterile manner with mixed cultures of methanotrophs. The method also preferably uses periodic biomass-wasting (PHA harvesting) at the end of the carbon feed phase, gradually lengthening the time period of carbon deprivation phase to create a penalty for rapid PHA degradation and incentive for PHA accumulation. Also, bacterial enrichment cultures may be introduced periodically. The PHA-accumulating bacteria are preferably grown on common anaerobic degradation products, specifically volatile fatty acids, such as acetate and propionate, and methane gas. The PHA has useful applications in bioplastics and other products.

12 Claims, 5 Drawing Sheets

200 Landfill

250 Anaerobic digester

USE OF SELECTION PRESSURES TO ENABLE MICROBIAL BIOSYNTHESIS OF POLYHYDROXYALKANOATES FROM ANAEROBIC DEGRADATION PRODUCTS

CROSS-REFERENCE TO RELATED APPLICATIONS

This application claims priority from U.S. Provisional Patent Appl. No. 61/133,056 filed on Jun. 24, 2008, which is incorporated herein by reference.

FIELD OF THE INVENTION

This invention relates generally to methods for microbial biosynthesis of biopolymers. More specifically, it relates to improved biosynthesis of polyhydroxyalkanoates.

BACKGROUND OF THE INVENTION

As environmental concerns increase over the production and disposal of conventional petrochemical-based plastics, there is a growing incentive to find a simple method of producing inexpensive alternatives.

Bioplastics have numerous advantages over petrochemical-based plastics. Unlike petrochemical-based plastics, bioplastics rapidly biodegrade and are non-toxic. Bioplastics are derived from renewable resources, decreasing demand for non-renewable petrochemical resources. Bioplastics have lower energy inputs than petrochemical-based plastics, and their production results in lower $CO_2$ emissions than petrochemical plastic production. It is therefore of great interest to find improved methods for producing bioplastics.

Bioplastics may be produced using various biopolymers such as polyhydroxyalkanoates (PHA), and particularly the polymer of hydroxybutyrate, polyhydroxybutyrate (PHB). PHAs are polyesters with repeating subunits (100-30,000) that have the formula

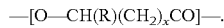

—[O—CH(R)(CH$_2$)$_x$CO]—.

The most common type of PHA is PHB, where R=CH$_3$ and x=1. Another is polyhydroxy valerate (PHV), where R=CH$_2$CH$_3$ and x=1.

PHAs are produced by many bacteria under unbalanced growth conditions when they have access to surplus carbon but lack an essential nutrient, such as phosphorus, nitrogen, sulfur, iron, sodium, potassium, magnesium, or manganese. Under these conditions, the bacteria hoard the carbon, storing it as intracellular PHA granules. The granules are consumed when supplies of carbon and energy become limiting or when the limiting nutrient again becomes available.

The most common known methods of PHA production use pure cultures, relatively expensive fermentable substrates, as sugar from corn, and aseptic operation. The price of PHA produced using this feedstock and methodology currently exceeds the price needed to be competitive with petrochemical-based plastics. Thus, an important challenge is to provide improved methods for producing PHAs that are more efficient and less expensive, so that bioplastics can become commercially competitive with petrochemical-based plastics.

Some methanotrophs have been shown to produce PHBs from methane under nutrient limited conditions. The PHB-producing potential of most methanotrophic species, however, remains largely unexplored, as are methods for efficient and inexpensive biosynthesis of PHB.

SUMMARY OF THE INVENTION

In one aspect, the invention provides a method for PHA biosynthesis. Specifically, the method includes operating a sequencing bioreactor in alternating phases of nutrient deprivation and carbon feedstock deprivation to select for robust PHA-producing microbes. Preferably, the method includes operating the bioreactor in a non-sterile manner, periodic biomass-wasting (PHA harvesting) at the end of the carbon feed phase, gradually lengthening the time period of carbon deprivation phase to create a penalty for rapid PHA degradation and incentive for PHA accumulation, and/or periodically introducing bacterial enrichment cultures. The PHA-accumulating bacteria are preferably grown on common anaerobic degradation products, specifically volatile fatty acids, such as acetate and propionate, and methane in biogas. Continuous or sequencing batch reactors are operated under non-sterile conditions so as to create selection conditions favorable for organisms that accumulate PHA. A selective advantage is conferred upon PHA-accumulating microorganism by repeatedly cycling through the two periods, or stages. In the first stage the carbon source (i.e., volatile fatty acids and/or biogas methane) is present in excess but nutrients are absent. In the second stage nutrients are present but the carbon source is absent. During the first stage, PHA-producing bacteria accumulate PHAs, and during the second stage the organisms that accumulated PHAs are able to produce protein and replicate while cells that did not store PHA are unable to produce protein and replicate because they lack carbon. Repeated cycling between these two stages selects for microorganisms that produce PHA in order to replicate during the period of carbon starvation. PHA is preferably harvested from the biomass at the end of the carbon feed stage.

The cost of producing PHA using low-cost carbon sources (the products of anaerobic degradation, such as volatile fatty acids or biogas methane) and a nonsterile process is lower than previous production methods. Long-term, evolutionary advantages are also realized. Bioreactors that can operate under conditions that select against microorganisms that do not produce PHA enable non-sterile production of PHAs and, over the long term, tend to select for organisms that can store PHAs at high levels.

DETAILED DESCRIPTION

In the present description, the term "biodegradation" is defined as a breaking down of organic substances by living organisms, e.g., bacteria. In the present context, biodegradation is intended to include anaerobic fermentation. Similarly, "biosynthesis" is defined as a production of chemical compounds from simpler reagents by living organisms, e.g., bacteria.

To understand the conditions required for PHA production, it is helpful to define the terms "growth", "balanced growth", and "unbalanced growth". "Growth" is defined as an increase in cell mass. This may occur through cell division (replication) and the formation of new cells during "balanced growth", or, during "unbalanced growth", when cellular mass increases due to the accumulation of a polymer, such as PHA. In the latter case, growth may be manifest as an increase in cell size due to the accumulation of biopolymer within the cell.

During balanced cell growth, all of the feedstocks (electron donors and electron acceptors) and all of the nutrients are present in the ratios required to make all of the macromolecular components of the cell. No feedstock or nutrient limits the synthesis of proteins, complex carbohydrate polymers, fats, or nucleic acids.

During unbalanced cell growth, a feedstock or nutrient needed to make one or more of the macromolecules is not present in the ratio required for balanced growth. This feedstock or nutrient therefore becomes limiting, and is termed the "limiting nutrient". Some cells may still achieve net growth under these conditions, but the growth is unbalanced, with accumulation of polymers that can be synthesized in the absence of the limiting feedstock or nutrient. These polymers include intracellular storage products, such as the polydroxyalkanoates (PHAs)-polyhydroxybutyrate (PHB), polyhdroxyvalerate (PHV), and polyhydroxyhexanoate (PHHx)-glycogen, or secreted materials, such as extracellular polysaccharide.

As an example of balanced and unbalanced growth conditions consider the nitrogen requirement for balanced cell growth. Nitrogen constitutes about 12% of dry cell weight. This means that in order to grow 100 mg/L cell dry weight, 12 mg/L of N must be supplied along with a feedstock and other nutrients in the required stoichiometric ratios. If other feedstock and nutrients are available in the quantities needed to produce 100 mg/L of cell dry weight, but less than 12 mg/L of N is provided, then unbalanced cell growth may occur, with accumulation of polymers that do not contain N. If N is subsequently provided, the stored polymer may serve as feedstock for the cell, allowing balanced growth, with replication and production of new cells.

In one aspect, the present invention provides a cost-effective method for the production of PHB using methane as a source of carbon. The methane is preferably derived from biodegradation of organic waste.

Figure 1:
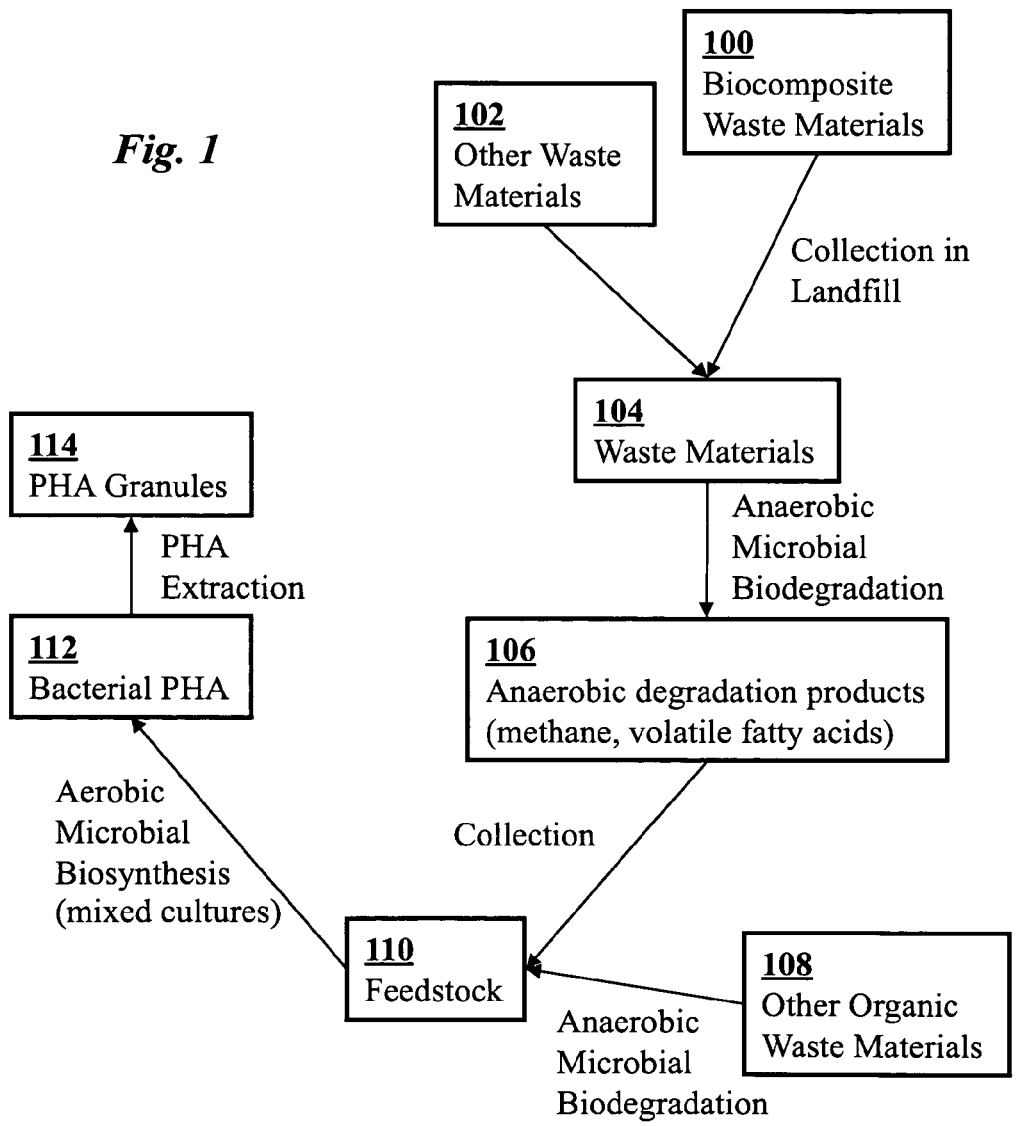
FIG. 1 is a flow diagram illustrating a biotransformation process which may employ the methods of the present invention.

FIG. 1 is an example of a biotransformation process which may employ the methods of the present invention as a part. Waste materials 104, which may include both biocomposite waste materials 100 as well as other organic solid waste materials 102 are collected in a modern landfill or anaerobic digester where they undergo anaerobic microbial biodegradation.

Figure 2A:
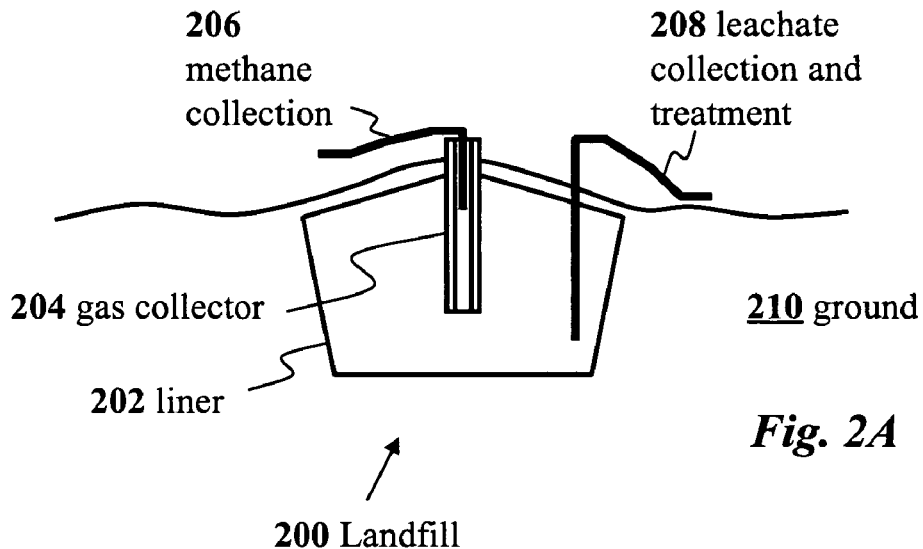
FIG. 2A is a schematic cross-sectional diagram of a landfill which may be used to produce feedstock for use in biosynthesis of PHA using methods of the present invention.

FIG. 2A illustrates a landfill 200 which may be used to biodegrade the waste materials. The landfill 200 is positioned in the ground 210 just below the surface. A liner 202 forms the walls of the landfill into which the organic waste such as biocomposite is placed. A methane gas collector 204 is used to collect methane degradation product of the biodegradation. The methane is then fed from the landfill using a methane collection tube 206. A tube 208 is used for leachate collection.

Figure 2B:
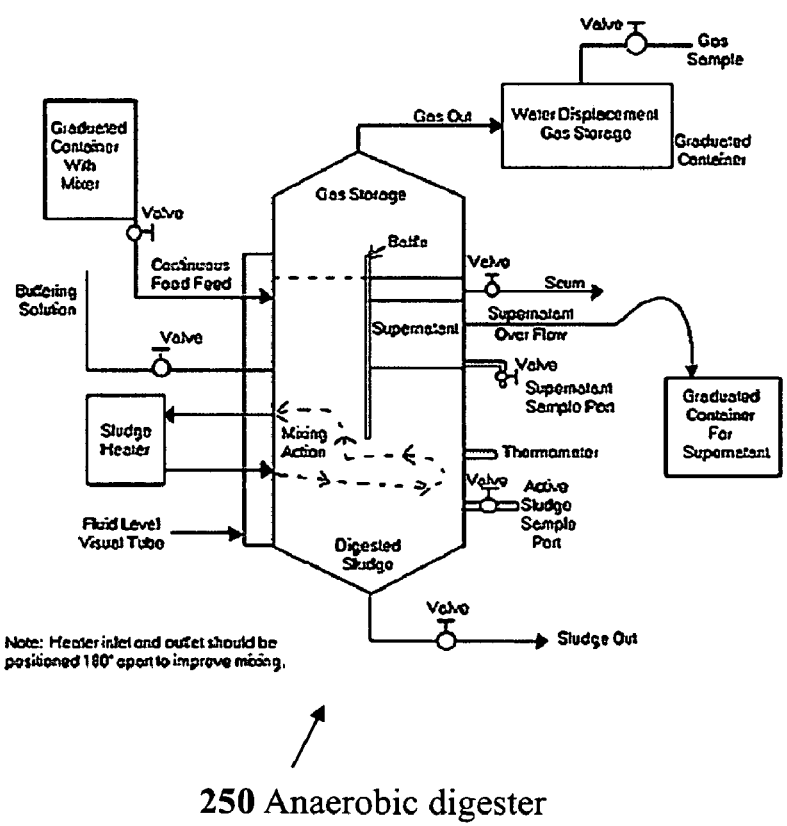
FIG. 2B is a schematic diagram of an anaerobic digester which may be used to produce feedstock for use in biosynthesis of PHA using methods of the present invention.

FIG. 2B illustrates a conventional anaerobic digester 250 which may be used for the biodegradation of waste materials to produce methane gas and digested sludge as anaerobic degradation products.

Returning to FIG. 1, anaerobic degradation products 106 of this biodegradation include methane and volatile fatty acids, e.g., acetic and propionic acids. The degradation products 106 are collected and may be stored temporarily and/or transported. In some cases the degradation products 106 may be combined with anaerobic fermentation products derived from other organic waste products 108, such as agricultural waste streams or treated wastewater, to form a feedstock 110 for subsequent biosynthesis of PHA. The feedstock may be used immediately, stored, or transported.

The use of methane and/or volatile fatty acids as a carbon source in the feedstock makes the biosynthesis process less expensive as compared with other microbial biosynthesis processes that use more expensive carbon sources. Methane also can be continuously generated and delivered to a batch culture as a uniform feedstock for growth of methanotrophs and PHA production. The feedstock 110 is used in aerobic microbial biosynthesis of PHA polymers 112 using a mixed bacterial community, preferably including methanotrophs. The PHA is grown under unbalanced growth conditions, i.e., when an essential nutrient is deficient or when toxic stressors are present. The biosynthesis may be performed using a small-scale fermentation facility.

PHA granules 114 are extracted from the biosynthesized bacterial PHA, e.g., using surfactant treatment to remove much of the protein followed by sodium hypochlorite digestion to remove most of the remaining protein, which leaves PHA granules intact. The alkaline waste stream that results from this process would likely be amenable to anaerobic digestion to methane, which could be collected and recycled as part of feedstock 110. Alternatively, other PHA granule extraction methods based on acid-base extraction and sonication may be used. PHA may also be recovered from cell debris by supercritical $CO_2$ extraction.

Mechanical properties of a PHA resin matrix can be altered through copolymerization with other hydroxylalkanoate monomers or with reactive polymer blending. For example, when PHB is copolymerized with hydroxylvalerate (HV) or hydroxyhexanoate (HHx), the ductility, toughness, and ease of molding increase while the crystallinity and melting point decrease.

The bacterial storage polymer poly-b-hydroxybutyrate (PHB) can be extracted and used as a biodegradable plastic for applications ranging from disposable eating utensils to furniture. Commercially, PHB granules have value as plastics or resins, with properties similar to petrochemical plastics.

We now turn to a more detailed description of certain specific techniques related to the method for biosynthesis of PHA.

Preferably, embodiments of the biosynthesis method use a bacterial community including a variety of methanotrophs that produce the highest levels of PHB (i.e., high ratios of grams PHB to grams biomass). This would specifically include the so-called "Type II" methanotrophs which use a carbon assimilation pathway that feeds into the biosynthetic pathway for PHB production. Other bacteria used in the biosynthesis of PHA are enriched by growth upon the specific biodegradation products 106 of the biodegradation process. The use of mixed bacterial cultures makes the process less expensive as compared with processes that use pure cultures by eliminating the need for maintenance of special cultures. In the context of the present description, the term "mixed cultures" is defined to include bacterial communities containing a variety of distinct cultures or species, irrespective of whether or not the species are well-defined. The term "mixed cultures" also includes enrichment communities. These are communities of organisms subjected to selective pressures favorable for the growth of organisms that positively affect PHA production and unfavorable for the growth of organisms that negatively affect PHA production.

The bacterial cultures may be derived from biomass from various sources. Methanotrophs are found in environments where both oxygen and methane are present, often at the interface between aerobic and anaerobic zones. They are common in rice paddies, swamps and marshes, surface sediments in ponds and lakes, activated sludge, and meadow and deciduous forest soils, including freshwater, brackish, and saline environments, deserts, landfills, coal mine surfaces, and oceans. Preferable sources include those environments subject to periodic stress, such as carbon, nutrient, or oxygen limitation. Environments with periodic stresses, such as intermittent availability of methane or water, are expected to select for methanotrophs that can store carbon for use during such times of stress. It is also likely that methanotrophs isolated from environments with these different selection pressures would have different rates and yields of PHB production.

Samples of methanotrophs from diverse environments may then be screened for their capacity to produce PHBs and to identify cultures capable of producing commercially significant levels of PHB.

Cultures may be grown to high density, subjected to nutrient limitation (e.g., nitrogen and phosphorus), and screened for PHA production in aerobic shake flask cultures. Methanotrophs are classified into three groups based on their carbon assimilation pathways and internal membrane structure: Type I (gamma proteobacteria), Type II (alpha proteobacteria), and a subset of type I known as Type X (gamma proteobacteria). Type I methanotrophs use the RuMP pathway for carbon assimilation whereas type II methanotrophs use the serine pathway. Type X methanotrophs use the RuMP pathway but also express low levels of enzymes found in the serine pathway. Type II methanotrophs accumulate PHB.

In one embodiment, methanotroph enrichments from different environments are introduced into a sequencing bioreactor with minimal media and forced to cycle between two phases: a first phase in which methane is supplied in excess while nitrogen is absent (or significantly reduced) and a second phase in which the flow of methane is stopped (or significantly reduced) and a pulse of nitrogen is added. This cycling is used to select for bacteria that store PHB when nitrogen is absent and subsequently use the PHB to produce new biomass when nitrogen is introduced to the system, thus conferring a competitive advantage on those organisms that produce higher quantities of PHB during the period of methane addition. Nitrogen is preferably selected as the limiting nutrient because its absence is known to induce PHB production and it can be easily monitored. Because the reactor is intrinsically designed to select for PHB-producing methanotrophs, it can be maintained as an open, non-sterile system, thus avoiding the costs and difficulties associated with maintaining a sterile culture during industrial production of PHB. Shifts in community composition may be monitored using a wide range of methods including terminal restriction fragment length polymorphism (T-RFLP) analysis of pmoA, clone libraries, and microarrays. System performance may be monitored by measuring the PHB content of the cells.

Preferably, a methane-fed culture grown to high cell density is used to produce high percentages of PHA when supplemented with acetate and/or propionate, and limited for nitrogen or phosphorus. The most effective culture is one with high PHA yield, high rate of PHA production, high growth rate, and high fitness, allowing robust non-sterile operation. This may be achieved by allowing communities to adapt to an environment that provides a selective advantage for PHA production. The biosynthesis may be performed in a bioreactor with conditions maintained to favor high levels of PHA production under non-sterile growth conditions in rapid, high cell density fermentations.

Figure 3:
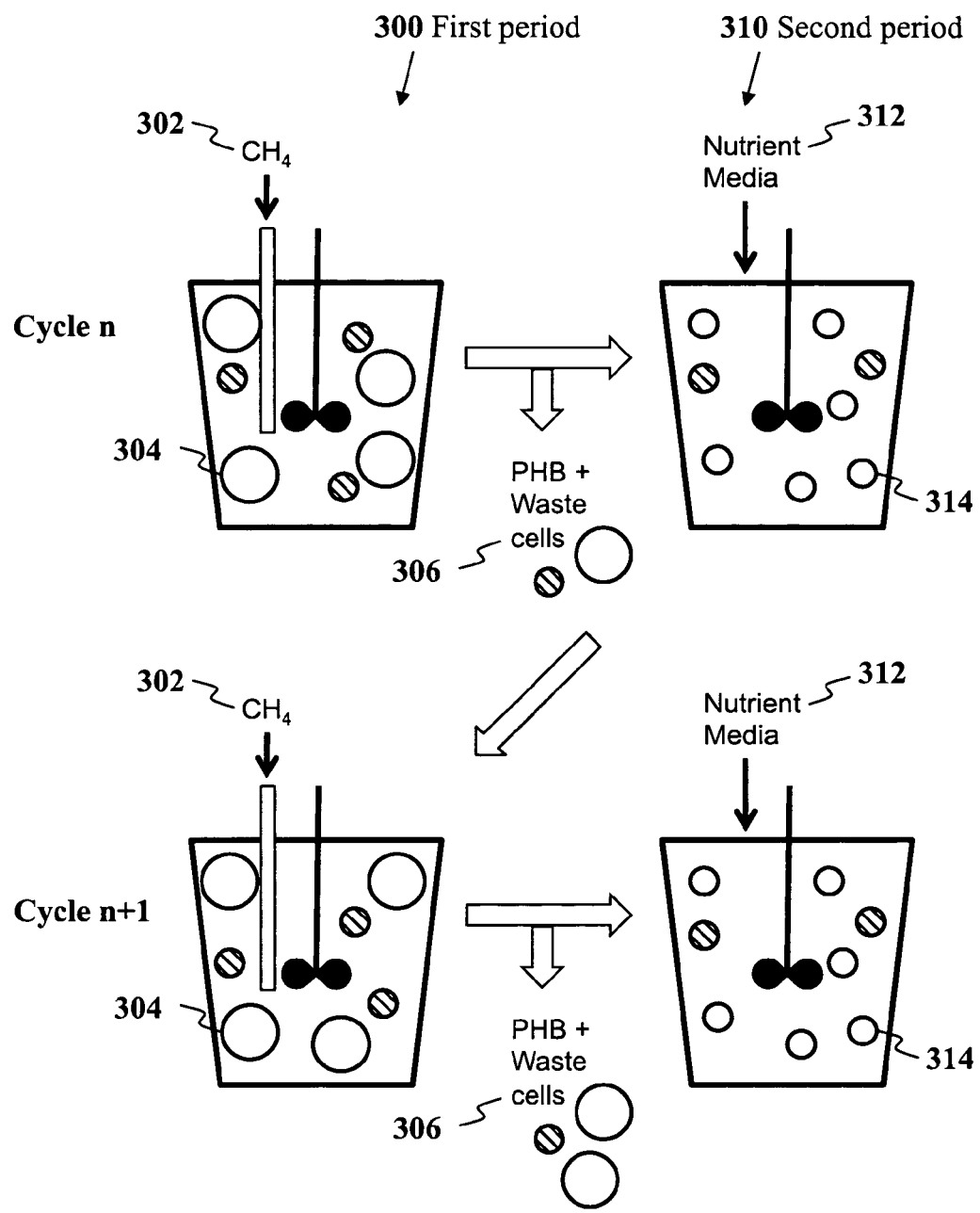
FIG. 3 is a schematic diagram illustrating two cycles in a sequence of bioreactor cycles in which each cycle includes a first period of carbon surplus and PHA production and a second period of carbon starvation and cell division, according to an embodiment of the invention.

A range of bioreactor configurations may be used, including sequencing membrane bioreactors and a continuous multistage dispersed growth configuration. Preferably, the bioreactor is operated to select for bacteria that efficiently produce PHB from methane, i.e., the bioreactor conditions select against bacteria that either do not produce PHBs from methane or produce them inefficiently. For example, as illustrated in FIG. 3, sequencing batch reactors can be operated by repeatedly cycling through two periods. Cycles n and n+1, each containing two periods, are shown. In the first period 300 of cycle n, methane 302 is provided in excess, but no nutrients. Methanotrophs 304 that are able to accumulate PHB under these conditions enlarge. At the end of the first period a portion of the bacteria are harvested as waste cells 306 and PHB is extracted. In the second period 310 nutrients 312 are provided but no methane. The bacteria 304 are able to use their stored PHB to replicate during this phase and to maintain cell function, while other bacteria 314 with smaller amounts of stored PHB will replicate less and are subject to cell decay as they cannot meet the energy demands for cell maintenance. The two periods are then repeated in cycle n+1, and so on. Repeated cycling through these periods will select for bacteria that produce enough PHB in the first period to replicate during the second period of carbon starvation. Additional species may be periodically introduced, e.g. at the beginning of the first period of a cycle. Organisms able to produce more PHBs more quickly should become dominant. Operating the system in a non-sterile manner ensures that the dominant species has a high relative fitness. Different methanotrophs will likely produce PHB with differing molecular weight distributions or potentially other PHA polymers. Consequently, the suitability of the PHA polymers for particular target applications serves as an additional criterion for subsequent selection of cultures.

Because the rate of cellular PHB utilization for growth is directly proportional to the PHB content of a cell, cells with a higher percent of dry weight as PHB will reproduce more quickly and species that accumulate a higher percentage of PHBs will have a selective advantage over other species. This advantage can be accentuated by gradually lengthening the time period without methane, creating a penalty for rapid PHB degradation and an incentive for PHB accumulation. In activated sludge systems, bacteria respond to periods of substrate excess ("feast") and deficiency ("famine") by storing PHBs during the substrate excess period and using them to make new cells during the substrate deficient period. The term "excess" in this context means that the feedstock and all other nutrients (except a limiting nutrient) are present at a level sufficient for balanced growth. The term "limited" or "deficiency" in this context means that a nutrient is present at a level that is less than needed for balanced growth. During a feedstock limitation, sufficient nutrients are present when there is enough to deplete the polymer previously stored under unbalanced growth conditions. The exact amount will depend on the amount of polymer storage that has occurred.

In addition to creating an environment that selects for methanotrophic species that produce PHBs, evolution of dominant species may occur as mutations confer selective advantages on daughter strains that outcompete the parent strains. Operation is expected to evolve a robust, PHB-producing methanotroph or a mixed culture that is better able to produce PHBs than the parent culture. Species compete against one another in an environment designed to select for the desired characteristics.

As shown in FIG. 3, a set of sequencing batch reactors may be operated to select for organisms that accumulate PHBs rapidly and at high yield and to enable competition of different species of PHB-producing methanotrophic bacteria. Operation may be managed so that PHB-producing bacteria have a selective advantage over those that do not. This may be accomplished by sequencing through two periods; a first period in which methane is present in excess but nutrients are absent and a second period in which nutrients are present but methane is absent. During the first period, PHB-producing bacteria accumulate PHBs; during the second period, the organisms that accumulated PHBs are able to produce protein and replicate while cells that did not store PHB are unable to replicate because they lack carbon. Repeated cycling between these phases with periodic biomass-wasting at the end of the methane feed period select for bacteria that produce enough PHBs to replicate during the period of carbon starvation.

The reactor sequences between periods of carbon excess with methane provided, and periods of carbon starvation with nutrients provided. Also shown is the effect of competition in successive cycles where the red cells are unable to accumulate significant quantities of PHB and thus are not able to replicate in the nutrient-sufficient phase.

In some embodiments, the system is inoculated with a promising enrichment. Additional species and mixed cultures are periodically introduced, at concentrations comparable to the concentration of the cells in the reactor. Prior to the addition of new cultures, an additional fraction of the existing cells are wasted. The PHB content of the wasted cells are then measured using a spectrofluorometric assay and the relative abundance of species is monitored by T-RFLP analysis. Organisms that are able to produce more PHBs more quickly and to a higher level become dominant. By operating the system in a non-sterile manner, the dominant species has a high relative fitness and has characteristics that would be desirable in an industrial system. Regularly obtained samples may be archived to permit detailed analyses of shifts in community structure that may correspond to enhancements or changes in PHB production.

PHAs from the most promising cultures may be characterized for monomer composition, molecular weight distribution, and other parameters important to bioplastic applications. The results of these studies may assist in the identification of cultures and strains for optimization of bioreactor operation and scale-up.

Information on phylogeny can be used to identify organisms, determine ecological relationship, and optimize PHB production.

Desired reactor configurations and operation select for the most promising culture that will enable high levels of PHA production with minimal energy inputs. Also of interest are cultures that produce PHA polymer blends or copolymers that are particularly well suited for specific applications.

Figure 4:
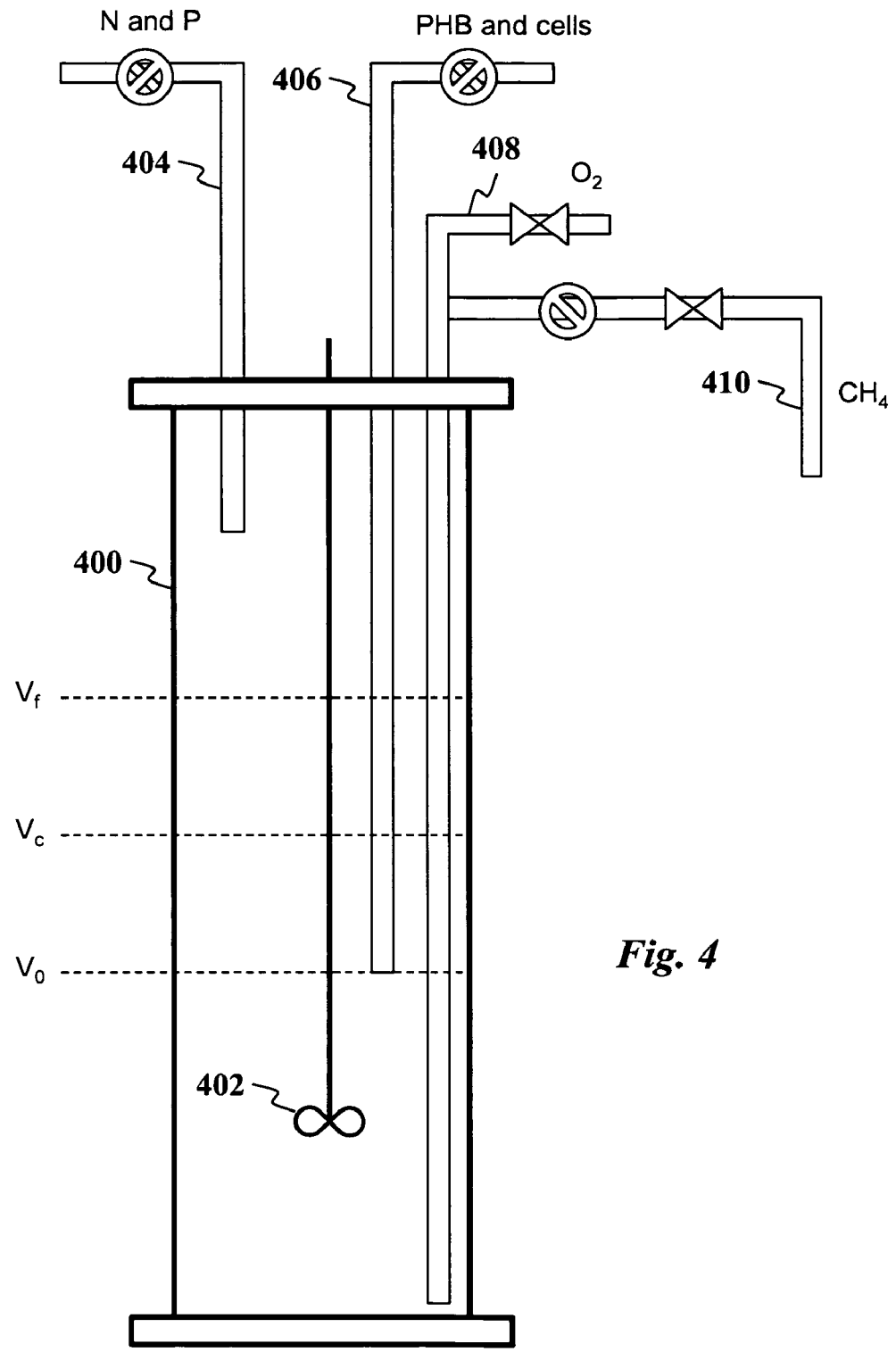
FIG. 4 is a schematic diagram illustrating a sequencing batch reactor for PHB production from methane according to an embodiment of the invention.

FIG. 4 illustrates another embodiment of a sequencing batch reactor for PHB production from methane. This design provides pH, DO (mixing), and temperature control. The reactor includes a vessel 400, a mixer 402, a valved nutrient inlet 404, a valved PHB and waste outlet 406, an oxygen inlet 408, and a valved methane inlet 410.

According to one method of PHB production, during a first period, nutrients (e.g., N and P) are added through opened inlet 404 while methane inlet 410 and harvesting outlet 406 are closed. The mixture volume increases during this period, causing the mixture level in the reactor to rise from the base level $V_0$. In a second period, methane is added through open inlet 410 and PHB accumulates while nutrient inlet 404 are harvesting outlet 406 are closed. The mixture volume increases further during this period, causing the mixture level in the reactor to rise to the full level $V_f$. Although no nutrients are added in the second period, some residual nutrients may still be present in the reactor. In a third period, the cultures are harvested by extracting PHB and waste cells from open harvesting outlet 406 while the nutrient inlet 404 and methane inlet 410 are closed. The volume decreases during this final period, dropping down from level $V_f$ to the base level $V_0$. The cycle then repeats.

According to another method of PHB production, during a first period, nutrients (e.g., N and P) are added through opened inlet 404 while methane inlet 410 and harvesting outlet 406 are closed. The mixture volume increases during this period, causing the mixture level in the reactor to rise from the base level $V_0$ to level $V_c$. In a second period, nutrients are added through opened inlet 404 and methane is added through open inlet 410 while harvesting outlet 406 is closed. The mixture volume increases further during this period, causing the mixture level in the reactor to rise from level $V_c$ to the full level $V_f$. In a third period, methane is added through open inlet 410 while PHB accumulates in the cells. In a fourth period, the cultures are harvested by extracting PHB and waste cells from open harvesting outlet 406 while the nutrient inlet 404 and methane inlet 410 are closed. The volume decreases during this final period, dropping down from level $V_f$ to the base level $V_0$. The cycle then repeats.

According to another technique of the invention, cell mass may be extracted from the sequencing reactor, then the extracted portion grown with complete nutrients to increase cell density, and then subjected nutrient limitation. This procedure involves taking samples from the reactor and using the samples for batch incubations to produce PHB.

Bioreactors may range from small bench-scale bioreactors to large-scale commercial production bioreactors, and also be of various types, including sequencing membrane bioreactors and a continuous multistage dispersed growth configuration. In larger scale bioreactors (i.e., fermentation volumes of tens of liters or more) mass transfer of poorly soluble gases (methane and oxygen) may be improved by delivery under pressure or via "dry" fermentations using gas phase delivery of methane and oxygen, and cell densities may be increased using ultrafiltration membrane modules (hollow fiber or flat sheet) for cell separation and concentration.

EXAMPLE

By way of illustration of the principles of the present invention, a specific example of PHB production using a bench-scale bioreactor will be described. A bench-scale bioreactor (1 L working volume) was cycled daily between periods of 1) methane addition and nitrogen starvation (~16 hours) and 2) methane starvation with nitrate addition (~8 hours). A small fraction of the volume (~50 mL) was sampled twice daily, at the beginning of each period, and was replaced with equivalent media daily. The wasted cells were frozen for analysis of biomass and PHB concentration. The concentration of nitrate in the reactor was monitored daily. Biomass pellets were archived throughout the experiment. DNA was later extracted from these pellets and Terminal Restriction Fragment Length Polymorphism (T-RFLP) with the restriction enzyme Alu I was used to characterize the community within the reactor.

The bioreactor was inoculated with a methanotroph enrichment culture that had previously been shown to produce ~30% PHB under nutrient limitation. After inoculation, the reactor was maintained under non-sterile conditions. No additional cultures were intentionally introduced into the system.

This experiment demonstrated that a PHB-producing methanotrophic culture can be maintained under the previously described cycling conditions for a period of 59 days. The levels of biomass within the system were controlled by the nitrate addition and additional wasting events. The PHB content of the cells (g PHB/g total biomass) fluctuated throughout the experiment but typically remained above 20%.

T-RFLP analysis showed that the community within the reactor was relatively stable. A detailed analysis of individual cycles shows that the PHB content of the system fluctuated daily as expected: PHB content increased during the period of methane addition/nitrogen starvation and decreased during the period of methane starvation/nitrogen addition.

CONCLUSION

This method selects for PHA-accumulating bacteria grown on common anaerobic degradation products, specifically volatile fatty acids, such as acetate and propionate, and methane gas. Continuous or sequencing batch reactors are operated under non-sterile conditions so as to create selection conditions favorable for organisms that accumulate PHA. A selective advantage is conferred upon PHA-accumulating microorganism by sequencing through two stages a first stage in which the carbon source (i.e. volatile fatty acids and/or methane) is present in excess but nutrients are absent and a second stage in which nutrients are present but the carbon source is absent. During the first stage, PHA-producing bacteria accumulate PHAs during the second stage, the organisms that accumulated PHAs are able to produce protein and replicate while cells that did not store PHA are unable to produce protein and replicate because they lack carbon. Repeated cycling between these phases selects for microorganisms that produce PHA in order to replicate during the period of carbon starvation. PHA is harvested from the biomass at the end of the carbon feed period or stage.

Figure 5:
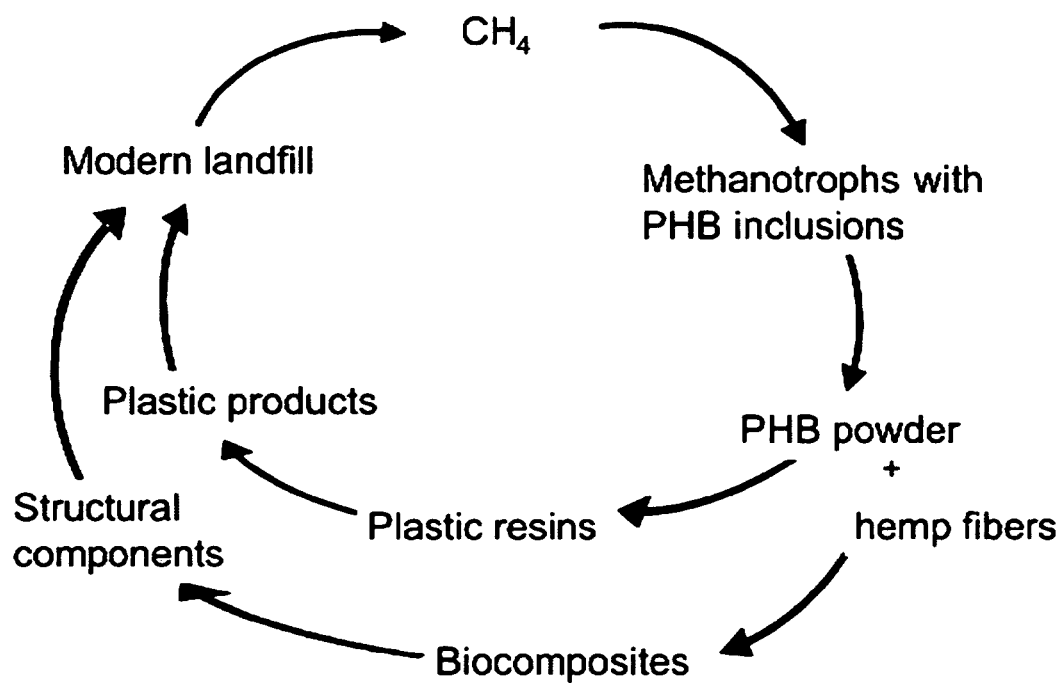
FIG. 5 is a flow diagram illustrating a carbon cycle which may use the methods of the present invention for the step of transforming methane into PHB.

Using the present methods, bioreactors can operate under conditions that select against microorganisms that do not produce PHA, enabling non-sterile production of PHAs and, over the long term, tend to select for organisms that can store PHAs at high levels. The cost of producing PHA using low-cost carbon sources (e.g., products of anaerobic degradation, particularly, methane) and a nonsterile process is expected to be lower than previous production methods. Methane is widely available at low cost, and it is the major product of anaerobic degradation of organic wastes. Moreover, under anaerobic conditions such as those inside a wet landfill or an anaerobic digester, organic wastes including PHB-containing products degrade to methane. Aerobic methane-consuming bacteria can convert methane into PHB, completing a "cradle-to-cradle" carbon cycle, as shown in FIG. 5. Projected benefits of this cycle include decreased pollution and aesthetic nuisance caused by petrochemical plastics, additional incentives for capture of methane (a major greenhouse gas), decreased $CO_2$ emissions, decreased energy usage, decreased dependence on petrochemicals, decreased demand for wood, and extended landfill life.

The invention claimed is:

1. A method for producing PHA polymers, the method comprising:
    performing in a bioreactor aerobic microbial biosynthesis of PHA polymers from a feedstock using mixed bacterial cultures in non-sterile conditions, wherein the feedstock comprises anaerobic degradation products;
    extracting the biosynthesized PHA polymers to obtain PHA granules; and
    repeatedly cycling the bioreactor through a first period and a second period;
    wherein the first period comprises maintaining in the bioreactor excess feedstock and limited nutrients;
    wherein the second period comprises maintaining in the bioreactor nutrients but limited feedstock and one of the following methods:
    (a) wherein the anaerobic degradation products comprise methane;
    or
    (b) wherein repeatedly cycling the bioreactor through the first period and the second period selects for organisms that stored PHAs in the first period while selecting against organisms that did not store PHA in the first period;
    or
    (c) wherein the anaerobic degradation products comprise methane and wherein repeatedly cycling the bioreactor through the first period and the second period selects for organisms that stored PHAs in the first period while selecting against organisms that did not store PHA in the first period.

2. The method of claim 1 wherein the anaerobic degradation products comprise methane.

3. The method of claim 1 wherein the anaerobic degradation products comprise volatile fatty acids.

4. The method of claim 3 wherein the volatile fatty acids comprise acetic and propionic acids.

5. The method of claim 1 wherein the nutrients comprise nitrogen.

6. The method of claim 1 wherein the nutrients comprise phosphorus.

7. The method of claim 1 further comprising harvesting PHA periodically from the bioreactor.

8. The method of claim 7 wherein the harvesting is performed at the end of the first period.

9. The method of claim 1 wherein repeatedly cycling the bioreactor through the first period and the second period comprises gradually increasing a duration of the second phase.

10. The method of claim 1 wherein the mixed bacterial cultures comprise methanotrophic bacteria.

11. The method of claim 1 further comprising periodically introducing into the bioreactor additional microbial species.

12. The method of claim 1 wherein repeatedly cycling the bioreactor through the first period and the second period selects for organisms that stored PHAs in the first period while selecting against organisms that did not store PHA in the first period.

* * * * *